United States Patent
Irion et al.

(10) Patent No.: US 8,409,082 B2
(45) Date of Patent: Apr. 2, 2013

(54) VIDEO ENDOSCOPE WITH SWITCHABLE SEMICONDUCTOR LIGHT SOURCES

(75) Inventors: Klaus-Martin Irion, Emmingen-Liptingen (DE); Peter Schwarz, Tuttlingen (DE)

(73) Assignee: Karl Storz GmbH & Co. KG (DE)

( * ) Notice: Subject to any disclaimer, the term of this patent is extended or adjusted under 35 U.S.C. 154(b) by 868 days.

(21) Appl. No.: 12/498,616

(22) Filed: Jul. 7, 2009

(65) Prior Publication Data
US 2010/0022829 A1    Jan. 28, 2010

(30) Foreign Application Priority Data
Jul. 7, 2008  (DE) .......................... 10 2008 033 506

(51) Int. Cl.
*A61B 1/06* (2006.01)
*G02B 6/42* (2006.01)

(52) U.S. Cl. ........ 600/178; 600/182; 362/572; 362/574; 385/25; 385/26

(58) Field of Classification Search .................. 600/132, 600/178, 182; 362/572, 574; 385/25–26
See application file for complete search history.

(56) References Cited

U.S. PATENT DOCUMENTS

| | | | |
|---|---|---|---|
| 4,512,627 A * | 4/1985 | Archer et al. .................. 385/20 |
| 4,569,334 A * | 2/1986 | Ohshiro ........................ 600/182 |
| 4,753,501 A | 6/1988 | Battle | |
| 4,905,082 A * | 2/1990 | Nishigaki et al. ............. 348/73 |
| 5,413,573 A * | 5/1995 | Koivukangas .................. 606/1 |
| 5,949,929 A * | 9/1999 | Hamm ............................ 385/25 |
| 6,097,423 A | 8/2000 | Mattsson-Boze et al. | |
| 6,128,426 A | 10/2000 | Einhorn | |
| 6,135,947 A * | 10/2000 | Watanabe et al. ............. 600/178 |
| 6,332,891 B1 * | 12/2001 | Himes ............................ 606/169 |

(Continued)

FOREIGN PATENT DOCUMENTS

| | | |
|---|---|---|
| CH | 604193 A5 | 8/1978 |
| DE | 3914825 C1 | 9/1990 |

(Continued)

OTHER PUBLICATIONS

European Search Report; EP 09 16 4614; Sep. 16, 2009; 9 pages.

*Primary Examiner* — John P Leubecker
*Assistant Examiner* — Arnaldo Torres Diaz
(74) *Attorney, Agent, or Firm* — St. Onge Steward Johnston & Reens LLC (57) ABSTRACT

A video endoscope has an endoscope part having a central image signal conductor, at least one optical waveguide, and a light supplying part which can be coupled to a proximal end of said endoscope part. The light supplying part has a central image signal conductor connection at a distal end thereof, and a light supply arranged coaxially around said central image signal conductor connection. The light supply has a plurality of light-emitting elements, each of said light-emitting elements can be supplied by means of a switchable semiconductor light source. Position sensors are arranged in an area of said light-emitting elements, and position indicators are arranged in an area of said optical waveguide. A position of said position indicators can be detected by said position sensors when said endoscope part and said light supplying part are coupled. Based on a detection of said position indicator, at least those light-emitting elements lying opposite to said optical waveguide are activated.

21 Claims, 3 Drawing Sheets

U.S. PATENT DOCUMENTS

| | | | |
|---|---|---|---|
| 6,342,061 B1 * | 1/2002 | Kauker et al. | 606/180 |
| 6,443,888 B1 * | 9/2002 | Ogura et al. | 600/132 |
| 7,290,915 B2 * | 11/2007 | Solovay et al. | 362/580 |
| 7,361,140 B2 * | 4/2008 | Ries et al. | 600/132 |
| 7,695,429 B2 * | 4/2010 | Hino | 600/132 |
| 7,762,950 B2 * | 7/2010 | Hirata | 600/179 |
| 7,982,199 B2 * | 7/2011 | Deshays | 250/504 R |
| 2002/0137987 A1 * | 9/2002 | Watanabe et al. | 600/178 |
| 2003/0185487 A1 | 10/2003 | Fernando et al. | |
| 2006/0206003 A1 * | 9/2006 | Hoeg et al. | 600/112 |
| 2008/0300456 A1 * | 12/2008 | Irion et al. | 600/109 |
| 2009/0086213 A1 * | 4/2009 | Masuda | 356/479 |

FOREIGN PATENT DOCUMENTS

| | | |
|---|---|---|
| DE | 19621370 A1 | 7/1997 |
| DE | 19715510 A1 | 10/1998 |
| JP | 62258408 A | 11/1987 |
| WO | 2006108143 A2 | 10/2006 |

* cited by examiner

Fig.5

VIDEO ENDOSCOPE WITH SWITCHABLE SEMICONDUCTOR LIGHT SOURCES

BACKGROUND OF THE INVENTION

The invention relates to a video endoscope, comprising an endoscope part, which has proximally a central image signal conductor and at least one optical waveguide, and a light supplying part, which can be coupled to the endoscope part and which has distally a central image signal conductor connection and a light supply arranged coaxially around the image signal conductor connection in the coupling area, wherein endoscope part and light supplying part are rotatable with respect to one another.

A video endoscope of this type is known from German Patent DE 39 14 825 C1.

In the case of such video endoscopes having two components that can be coupled to one another, for ergonomic reasons one requirement demands that, in the course of coupling, the image conducting or image transmission system and the light guiding or light transmission system be coupled in one operation. The separate coupling of fibre-optic cable and camera at different interfaces is time-consuming and laborious. Moreover, two separate cables are necessary, which usually issue in different directions which requires more space and conceals more view in the field of the surgical operation.

Systems of a universal coupling in which light and image are coupled in one go have therefore been developed.

One such coupling system, as provided by the Applicant, is described in German Patent Application DE 197 15 510 A1, wherein projecting axially from the endoscope part there is a first pin, which contains the image conducting system, and a further pin containing the light guiding system extends parallel thereto.

These two pins are inserted into corresponding depressions in the camera part, thereby ensuring an exactly aligned orientation of image conducting system and light guiding system in conjunction with a simple coupling operation.

What is disadvantageous about this system is that light and image are coupled rigidly, i.e. non-rotatably.

In numerous endoscopes, particularly in rigid endoscopes, usually the viewing direction is not implemented exactly in the longitudinal axis of the shaft the so-called 0° viewing direction, but rather in a manner deviating therefrom, for example in a 30° viewing direction. If, then, this endoscope is rotated during a surgical procedure, the image also necessarily rotates, for example, an image which is visualized on a monitor by the camera and which the surgeon observes. If the surgeon has carried out a 180° rotation in the body with the endoscope, for example, the image that he views would be upside down. However, since this is not desirable, rather surgeons want to see the image in the upright position, so-called image erecting systems have been developed and gained acceptance.

In the case of the rigid coupling, as described in German Patent Application DE 197 15 510 A1, this requires complex image erecting systems, as described, for example, in U.S. Pat. No. 6,097,423.

In the case of the video endoscope in German Patent DE 39 14 825 C1, as described in the introduction, the two coupled parts, namely the endoscope part and the camera part that feeds the illumination light, are rotatable. In this case, the image conducting or image transmission system is arranged centrally both in the endoscope part and in the camera part and is coupled at an interface.

At said interface, the light guiding system of the endoscope part is embodied in such a way that a ring of optical waveguides is arranged circumferentially around the central image conducting/image transmission system. A corresponding ring having an identical diameter is provided in the illumination light/camera part, which ring lies opposite the ring of optical waveguides of the endoscope part at the interface.

The optical waveguides usually comprise numerous thin optical fibres that are laid in a manner such that they are as far as possible bundled in the endoscope. These optical waveguide fibres have to be spliced to form the ring at the coupling place. The same correspondingly holds true for the camera part.

Accordingly, only those endoscope parts in which the spliced ring of optical waveguides corresponds exactly to the diameter of the ring at the camera part can be coupled to the camera part, since otherwise no illumination light can be transmitted.

In the case of small endoscopes having relatively thin shafts, the optical waveguides would then have to be spliced into a relatively large ring of optical waveguides at the interface, as a result of which, particularly in the case of small-calibre endoscopes, there is no possibility for optimal adaptation since the coaxial light ring required becomes relatively thin in the case of thin-calibre endoscopes and high coupling losses occur.

There is a need, however, for standard couplings both for large-calibre and for small-calibre endoscopes which contain a rotatable coupling for image erection, which simply and reliably enable the coupling operation in one go and which additionally exhibit optical waveguide coupling with the lowest possible coupling losses.

It is an object of the present invention, therefore, to further develop a video endoscope of the type mentioned in the introduction to the effect that a coaxial coupling of light and image is possible, where coupling losses are intended to be kept as low as possible, and a mechanically simple rotatability is possible.

SUMMARY OF THE INVENTION

This object is achieved by a video endoscope comprising an endoscope part having at a proximal end thereof a central image signal conductor, at least one optical waveguide, and a light supplying part which can be coupled to said proximal end of said endoscope part, said light supplying part has a central image signal conductor connection at a distal end thereof, and a light supply arranged coaxially around said central image signal conductor connection in a coupling area of said light supplying part, said endoscope part and said light supplying part are rotatable with respect to one another when coupled, wherein said light supply has a plurality of light-emitting elements arranged around said central image signal conductor connection, each of said light-emitting elements can be supplied by means of a switchable semiconductor light source; and wherein position sensors are arranged in an area of said light-emitting elements, and position indicators are arranged on said endoscope part in an area of said at least one optical waveguide, a position of said position indicators can be detected by said position sensors when said endoscope part and said light supplying part are coupled, and wherein, based on a detection of said position indicator by a position sensor, at least these light-emitting elements lying opposite to said optical waveguide are activated.

The basic concept consists, then, in configuring the coupling coaxially in such a way that the image information is coupled centrally. The plurality of light-emitting elements arranged around the image signal conductor connection can be activated individually in each case, to be precise, in a manner dependent on the position at which an optical waveguide or an optical waveguide connection is situated when the endoscope part is coupled. For this purpose, position sensors are respectively arranged in the region of the light-emitting elements, which position sensors detect the position of the optical waveguide at the endoscope part by means of its position indicator. As a result, it is possible, in the endoscope part, to place the optical waveguide connection at locations in the coupling area which are the most favorable for the construction of the endoscope part.

In the region of the location at which an optical waveguide, usually an optical waveguide bundle, ends at the endoscope part in the coupling area, a corresponding position indicator is present. Its position is detected by the light supplying part and at least those light-emitting elements of the light supplying part which lie opposite the optical waveguide at the coupling location are activated.

Semiconductor light sources, primarily LEDs and OLEDs, can be produced inexpensively and in desired geometrical forms and can be switched rapidly. A real light-emitting elements can therefore be provided, which are arranged around the central image signal conductor connection, in a manner distributed on the entire coupling area.

If the endoscope part is rotated, that is to say if its position relative to the light supplying part is altered, this is detected by the light supplying part and the light-emitting elements which now lie opposite the optical waveguide are activated. This ensures that at least those light-emitting elements which lie opposite the cross section of the optical waveguide connection of the endoscope are activated in any arbitrary rotation state. Furthermore, the transition bridges can also be illuminated as well.

This has the advantage not only that an optimum light source with low coupling losses is available in each rotation position, but also that it is possible for example to identify the radial distance of the optical waveguides from the central image signal conductor connection, that is to say whether endoscopes of different calibres or with different arrangements of the optical waveguide connection at the coupling location are present.

Alongside the light coupling, the image coupling is effected centrally. In the case of optical image guiding, the image signal conductor of the endoscope part is a rigid rod lens system or a flexible fibre image conducting system.

In video endoscopes, the image can be converted into an electrical signal by means of an electrical image converter. In particular, solid-state sensors such as CCD sensors or CMOS sensors are suitable as image converters.

The image signal conductor connection of the light supplying part is embodied such that, independently of the configuration of the light coupling of the endoscope part, the image signal thereof can be forwarded and/or converted. The light supplying part therefore contains an electrical image converter that converts an optical image signal supplied by the endoscope part into an electrical image signal. It is therefore a camera part.

In order that video endoscopes can also be coupled, in addition or as an alternative an electrical signal channel can be present, which forwards electrical image signals of the endoscope part.

The image signal conductor connection of the light supplying part therefore comprises an optical image signal conductor with electrical image converter and an electrical image signal conductor.

This enables high variability and flexibility with regard to the range of use of endoscope part, on the one hand, and light supplying part, on the other hand, which can nevertheless be coupled to one another in a standardized manner, however, wherein it is ensured that light coupling with low scattering losses is possible.

If, by way of example, there is an optical waveguide connection at the endoscope part with a relatively large cross section, such that a plurality of light-emitting elements are covered, it is possible to activate all of said elements for light emission which lie in the cross section of the optical waveguide. When the coupling is rotated, it is then also always ensured that at least all those light-emitting elements which lie in the region of the cross section of the optical waveguide connection or optical waveguide connections of the endoscope part are activated in any desired rotation position. Thus, an optimum illuminance is always present which is coupled into the optical waveguide. This can be realized as a result of the interplay of the position sensors at the light supplying part and the position indicator in the region of the optical waveguide at the endoscope part.

In a further configuration, only those light-emitting elements which lie in the cross-sectional area of an optical waveguide of the endoscope part are activated.

Every light-emitting element also simultaneously emits heat. If only those light-emitting elements which lie in the cross-sectional area of the optical waveguide in the endoscope part are activated, light is emitted only in the region at the light supplying part. As a result, it is possible to avoid not only unnecessary light losses but also an unnecessary thermal radiation which could lead to heating in the coupling area, which adversely influences other components, or disturbs the handling by the surgeon.

In addition, this is favorable in terms of the energy balance. This also opens up further possibilities in connection with ordered optical waveguide arrangements in the endoscope part, with the result that it is possible, in principle, to provide a structured lighting or illumination of the image field.

In a further configuration of the invention the individual light-emitting elements are embodied in segment-like fashion.

This measure has the advantage that the plurality of elements can be combined to form groups or patterns in order to cover regions in which the optical waveguides of the endoscope part can be situated.

In a further configuration of the invention, the light-emitting elements are combined to form at least one ring.

This measure has the advantage that, in the case of a specific radial position of an optical waveguide at the coupling area of the endoscope, in the entire 360° rotation range thereof, an uninterrupted light transmission is possible. By means of corresponding shaping of the segment-like light-emitting elements, the latter can be combined to form continuous illumination rings. In this case, it is also possible to realize a plurality of concentric illumination rings, such that, for example, in the case of an endoscope part in which the optical waveguide connection is arranged at a relatively large radial distance from the central image conductor connection, only a correspondingly radially outer illumination ring of the light supplying part has to be activated.

In a further configuration of the invention, the switchable semiconductor light sources are selected from the group consisting of LEDs, OLEDs, diode lasers or combinations thereof.

As already mentioned, these semiconductor light sources are very cost-effective and can be switched very rapidly, without the lifetime being significantly impaired thereby.

They can be produced in any geometrical forms, thus, for example, in annulus sections, with the result that the individual elements can be combined to form illumination rings running around the central image signal conductor connection.

In a further configuration of the invention, the switchable semiconductor light source directly constitutes the light-emitting element.

This measure has the advantage that said light-emitting elements are constructed in a very simple manner structurally, namely by virtue of the fact that they are mounted directly on the end face in the region of the coupling area at the light supplying part.

In a further configuration of the invention, the switchable semiconductor sources are arranged at a distance from the light-emitting element situated on the end side and are connected to said element via optical waveguides.

This measure has the advantage that the heat-emitting semiconductor light source lies somewhat remote from the actual coupling location, with the result that not only is it protected against mechanical influences in the region of the coupling location, but also the possibility of cooling the light source at this remote location is opened up. However, care must be taken to ensure that lowest possible coupling losses occur during the forwarding of the light to the light-emitting elements arranged at the coupling situated on the end side.

Moreover, this possibility, as a result of corresponding configuration of the optical waveguides and the light-emitting elements, opens up the ability to influence the light generated by the light source, for example, in the sense of a filtering, a polarization or the like. Thus, the light-gathering and forwarding elements can comprise optical fibres having different numerical apertures, whereby the image field can be illuminated differently, such that, e.g., a 3D depth perception can be produced by shadowing.

In a further configuration of the invention, the light-emitting elements emit light of different colors.

This possibility opens up varicolored illuminations and lighting in photodynamic diagnosis. In this case the subject to be examined is administered beforehand an agent which, by way of example, is absorbed to a greater extent by tumor tissue than by non-tumorous tissue. By means of irradiation with a specific wavelength range of a specific color, said tumor can be excited to particularly intensive fluorescence.

Consequently, the construction not only opens up standardized and secure couplings, but at the same time opens up examination measures such as photodynamic diagnosis.

In a further configuration of the invention, the semiconductor light sources are accommodated in a separate apparatus.

This measure has the advantage that, in the case of high-energy light, the semiconductor light sources are so far away from the coupling location that the heat emission associated therewith is greatly reduced. Moreover it is possible to correspondingly cool the semiconductor light sources, also in order to increase their lifetime, by way of example.

A further configuration correspondingly makes provision for providing a cooling system for cooling the semiconductor light sources.

In a further configuration of the invention, the position sensors and position indicators are embodied as Hall sensors.

Detecting a position on the basis of the principle of Hall sensors has become widely used in technology, and such sensors are therefore available in a cost-effective manner. Reliable position detection can thus be carried out, thereby ensuring that the optical waveguides in the endoscope part are optimally irradiated in each case.

It is also possible, of course, to choose other position sensors on the basis of optical effects or other effects. As already mentioned, however, Hall sensors are technologically very mature and available in an expedient manner.

In a further configuration of the invention, the endoscope part has an identification element, which can be read by means of a reading element arranged in the light supplying part.

This measure has the advantage that the type of endoscope part can be determined by means of the identification and e.g. the size, the position and number of the light-gathering bundles can thus be encoded. This results in an optimum driving of the light elements to be switched.

In a further configuration of the invention a latching mechanism is provided, which provides a latching of endoscope part and light supplying part in the coupled state.

This measure has the advantage that, by means of the latching mechanism, once the parts have been coupled to one another, they are connected to one another in a manner such that they are fixed in position axially, but are rotatable.

In a further configuration of the invention the latching mechanism is embodied in such a way that it is possible for the endoscope part to rotate about the light supplying part in positions with equidistant angular locations.

This measure has the advantage that positions of optimum light transmission can be assumed by means of the latching mechanism.

In a further configuration of the invention, the endoscope part has a control element, by means of which, when the light supplying part is detected, said endoscope part can be rotated about said light supplying part.

This measure has the advantage that the light supplying part can be held by one hand, and a rotation of the endoscope part can be carried out by one finger of the hand, by means of the control element. This permits a particularly ergonomic handling of the coupled parts, for example in the case of manually desired image erection.

In a further configuration of the invention, the light supplying part is embodied as a camera part with an electrical image converter.

This measure has the advantage that the light supplying part also constitutes the camera part, that is to say converts the optical signal into an electrical signal. This measure particularly has the advantage that standard endoscopes with optical light guiding, in particular the standard rigid endoscopes with lens optical waveguide systems, can be coupled to such a camera part.

In a further configuration of the invention, an electrical image converter is integrated in the endoscope part and a connector part is provided in the light supplying part, in order to forward the electrical image signal.

This measure has the advantage that the endoscope is configured as a camera part, that is to say as a video endoscope part having integrated image sensors. The image information of the endoscope part is already fed as an electrical signal to the light supplying part. A corresponding coupling location then has to be provided. This can be provided in standard fashion or be realized by an additional connector system.

In a further configuration of the invention, the light supplying part is embodied as a standing unit, into which the endoscope part can be inserted.

This measure is advantageous primarily in the case of semi-flexible or flexible endoscopes. This also opens up the possibility of additionally providing measures which make it possible for example to rotate the inserted endoscope part, in order to change over very deliberately to a different semiconductor light source, which has, for example, a different color temperature, a different numerical aperture, or else can simply serve as a replacement light source in the context of a partial defect.

In a further configuration of the invention, a drive is present in the light supplying part, by means of which drive a coupled endoscope part can be rotated.

This measure has the advantage that an automated rotation of the endoscope part about the longitudinal access thereof is possible. This opens up, through actuation of the drive, for example, an all-round view through 360° in the case of an optical assembly having a viewing direction that is different from 0° in order to carry out an orientation.

In a further configuration, the endoscope part has a central, proximally projecting pin, which accommodates the image signal conductor.

This measure has the advantage that the coupling process can be carried out mechanically simply in a targeted manner and reliably, namely by the projecting pin of the endoscope being able to be attached to the light supplying part in a targeted manner.

For this purpose, in a further configuration it is advantageous that the image signal conductor connection of the light supplying part has a cavity, into which the projecting pin can be inserted.

This measure has the advantage that this process can be carried out purposefully and reliably without relatively high attentiveness. Moreover, the image transmission or image coupling location is then situated remote from the light coupling location, with the result that an influencing of the transmitted image, particularly in optical systems, by scattered illumination light can be precluded.

The pin opens up further advantageous possibilities, namely, for example, of providing on said pin an identification element that is led past a corresponding reading element in the cavity during insertion. Clamping elements or the like can also be fitted to said pin in order to realize an additional protection against slipping, for example, if the latching mechanism has not yet latched into place.

Moreover, the pin can simultaneously serve as a guide during the rotary movement, with the result that no further measures are necessary in this regard.

It goes without saying that the features mentioned above and those yet to be explained below can be used not only in the combinations specified, but also in other combinations or by themselves, without departing from the scope of the present invention.

BRIEF DESCRIPTION OF THE DRAWINGS

The invention is described and explained in more detail below on the basis of some selected exemplary embodiments in association with the accompanying drawings, in which.

DETAILED DESCRIPTION OF PREFERRED EMBODIMENTS

Figure 1:
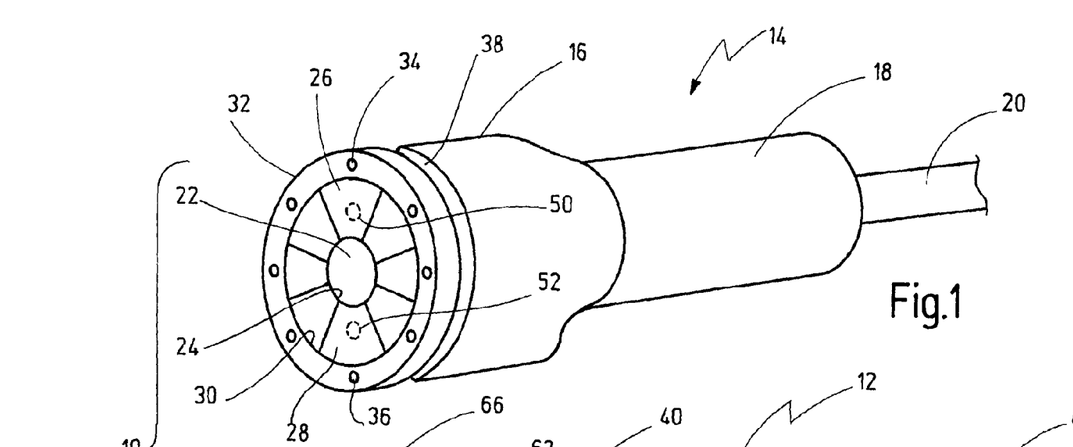
FIG. 1 shows a perspective view of the distal coupling end of a first embodiment of a light supplying part.
Figure 2:
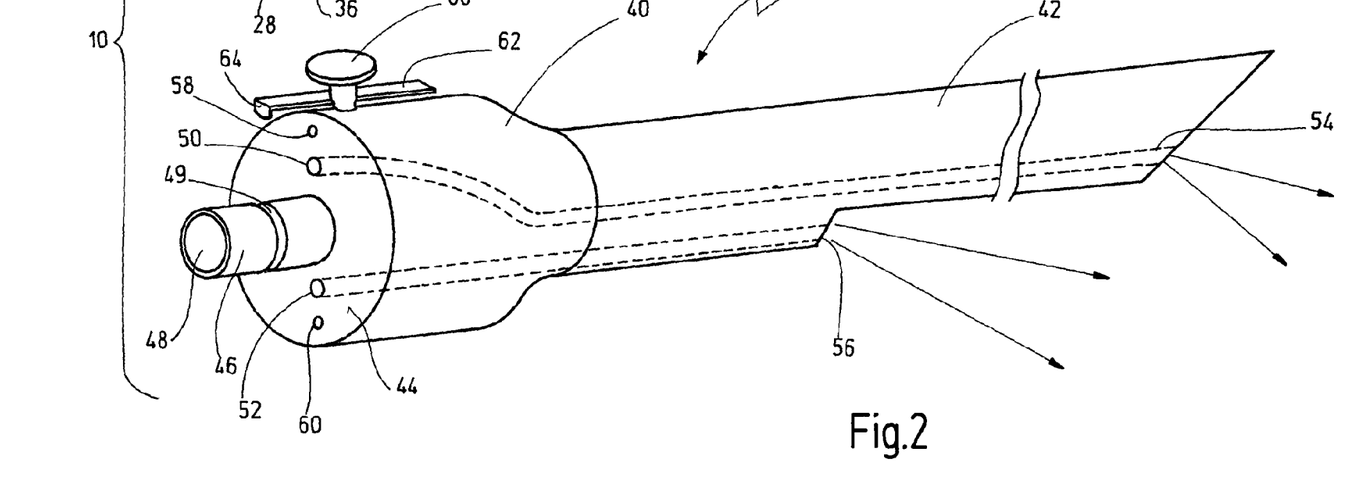
FIG. 2 shows a perspective view of the proximal coupling end of an endoscope part which can be coupled to the light supplying part from FIG. 1 to form a video endoscope.

A first embodiment of a video endoscope as illustrated in FIGS. 1 and 2 is designated in its entirety by the reference numeral 10.

The video endoscope 10 comprises an endoscope part 12 and a light supplying part 14.

The light supplying part 14 has a housing 16, which has proximally an approximately rod-shaped handle 18, by means of which the light supplying part 14 or the video endoscope 10 can be gripped by hand. Proximally, cables 20 that electrically supply or connect the components to be described below are led away.

Distally, a planar, approximately circular end face having an image signal conductor connection 22 centrally can be seen in FIG. 1.

The image signal conductor connection 22 has a cavity 24 approximately in the form of a blind hole, the point and purpose of which cavity will be described later.

A total of eight individual segment-like light-emitting elements are arranged around the cavity 24, in which case, for the sake of clarity, only two diametrically opposite elements 26 and 28 are designated by reference numerals. The geometrical configuration of the eight elements is such that when combined they produce an illumination ring 30. In the embodiment illustrated here, the eight elements are LEDs which can each be switched, i.e. activated for light emission, individually and independently of one another.

Around the illumination ring 30 there is a further ring body 32 in which a total of eight position sensors are inserted, in which case, for the sake of clarity here, too, only the two diametrically opposite position sensors 34 and 36 are provided with reference numerals. The distribution and arrangement of the eight position sensors is such that the latter are in each case located approximately centrally in the region of the outer circumferential edge of the respective light-emitting element.

To put it another way, a position sensor is also arranged in the region of each of the eight light-emitting elements. The point and purpose and also the circuitry function will be explained in greater detail below.

In the embodiment illustrated, the light supplying part 14 is embodied as a camera part, that is to say that an electrical image converter is arranged in the region of the bottom of the blind-hole-like cavity 24 of the image signal conductor connection 22, which electrical image converter converts an optical image fed via the image signal conductor connection 22 into an electrical signal. The latter is then forwarded via the cable 20 and visualized, for example, in a monitor (not illustrated here).

Spaced apart from the distal end in the proximal direction, a circumferential groove 38 is cut in the housing 16 of the light supplying part 14, in the bottom of which groove depressions are provided in a circumferentially uniformly distributed manner, in this case eight circumferentially uniformly distributed depressions. The point and purpose will likewise be explained later.

The endoscope part 12 illustrated in FIG. 2 is embodied as a rigid endoscope.

The endoscope part 12 has a head 40, which merges into an elongated rigid shaft 42.

The endoscope part 12 has a proximal end face 44, upon which a pin 46 projects centrally in the proximal direction. The length and the diameter of the pin 46 are chosen such that the latter can be pushed into the cavity 24 of the image signal conductor connection 22 of the light supplying part 14 in a matching manner. In the interior of the endoscope part 40, the pin continues as an optical channel extending as far as the distal end of the endoscope part 12. As usual in rigid endoscopes, an optical assembly is used therein which is composed of lenses, in particular rod lenses, and windows correspondingly situated on the end side.

This optical assembly forms an image signal conductor 48 and forwards an optical image signal.

As can furthermore be discerned from FIG. 2, the end face 44 is approximately of a size corresponding to the opposite end face of the light supplying part 14.

In the embodiment of the endoscope part 12 illustrated, two optical waveguides 50 and 52 are led from the proximal end face 44 to two light emission locations 54 and 56.

The optical waveguides 50 and 52 are each composed of a bundle of optical fibres, as is customary in endoscope construction.

The proximal ends of the optical waveguides 50 and 52 are arranged in such a way that they are arranged diametrically oppositely spaced apart from the pin 46.

Two position indicators 58 and 60 are arranged somewhat further outwards radially, the radial distance of which position indicators from the centre is chosen such that it corresponds to the radial distance of the position sensors 34 and 36 of the light supplying part 14.

Arranged on the outer side of the head 40 of the endoscope part 12 is a part of a latching mechanism, namely a lever latch 62, which exhibits a radially inwardly projecting latching lug 64 embodied in such a way that the latter can enter into the circumferential groove 38 on the light supplying part 14 or else additionally into the abovementioned depressions provided therein. A control element 66 is also provided centrally on the lever latch 62, the function of which control element will likewise be explained later.

A ring-shaped identification element 49, for example, in the form of a barcode, is placed around the outer side of the pin 46. A reading element (not visible here) is correspondingly arranged on the inner side of the cavity 24 of the image signal conductor connection 22, which reading element can read the barcode of the identification element 49.

In order to couple the components endoscope part 12 and light supplying part 14 to form the video endoscope 10, for example the light supplying part 14 is gripped by one hand by means of the handle 18 of said light supplying part. The endoscope part 12 is gripped by the other hand and the pin 49 of said endoscope part is pushed into the cavity 24 until the latching lug 64 of the lever latch 62 latches into the circumferential groove 38.

During this pushing-in process, the identification element 49 is led past the reading element, and read there, with the result that the information about which type of endoscope part 12 is involved, and possibly also which manufacturer, can be detected by means of the light supplying part 14. If this information comprises for example the fact that the endoscope part 12 is such an endoscope part that has two diametrically opposite optical waveguides 50 and 52 and if this information is available to a controller of the light supplying part 14, then circuitry measures can be implemented there, by which the activation of two diametrically opposite light-emitting elements is enabled, pre-programmed or processed in some other way.

If endoscope part 12 and light supplying part 14 are coupled to one another precisely in the orientation of FIGS. 1 and 2, the proximal end of the optical waveguide 50 is located in the region of the light-emitting element 26 and the optical waveguide 52 is located in the region of the light-emitting element 28, as indicated by dashed circles in FIG. 1. In this case, the position indicator 58 of the endoscope part 12 is located in the region of the position sensor 34 of the light supplying part 14. The position indicator 60 is correspondingly located in the region of the position sensor 36.

The position sensors and the position indicators are embodied as so-called Hall sensors. For this purpose, by way of example, the two position indicators 58 and 60 comprise permanent magnets, and the position sensors 34 and 36 generate an electric field. In the course of coupling, the position indicators 58 and 60 respectively approach the electric field of the position sensors; this can be detected. The circuit is chosen, then, such that precisely the two light-emitting elements 26 and 28 in the region of which the optical waveguides 50 and 52 are located after coupling are activated. In other words, light is generated and emitted effectively only where the light input sides of the optical waveguides 50 and 52 of the endoscope part 12 are situated.

On the basis of the construction illustrated, the endoscope part 12 is rotatable about the longitudinal axis of the light supplying part 14. This rotatability is firstly guided well by the central pin 46; for control purposes, one finger of the hand that has gripped the handle 18 can be placed onto the control element 66 and the rotary movement can be carried out by means of the latter. The latching lug 64 of the lever latch 62 then runs in the circumferential groove 38.

This rotation is desirable for example when the endoscope part 12, as in the exemplary embodiment illustrated, is not an endoscope having a rectilinear, that is to say 0°, viewing direction, but rather one having a deviating, for example 30°, viewing direction.

This rotatability permits a desired image erection of the video image generated by the light supplying part 14 if the endoscope part 12 has been rotated about its longitudinal axis. This is desirable, i.e. even if the endoscope part 12 has been rotated, an upright image is represented on the monitor.

Specific equidistant angular locations can be achieved by means of the above-described depressions in the bottom of the circumferential groove 38.

A particular advantage of the invention is manifested, then, in the fact that in the event of such rotation, this process can be detected and a corresponding reaction thereto can be effected in terms of illumination technology.

If the ends of the optical waveguides 50 and 52 are situated in the position illustrated in FIG. 1 and if the coupled endoscope part 12 is then rotated, in the clockwise direction in the view of FIG. 1, the optical waveguide 50 will leave the region of the light-emitting element 26 and enter into the element located next alongside the latter in the clockwise direction.

This is detected owing to the fact that the position indicator 58 leaves its opposite position relative to the position sensor 34 and approaches the position sensor located next in the clockwise direction. This can again be detected by the configuration as Hall sensors, with the result that after a rotation has been effected, for example, through 45°, the two light-emitting elements 26 and 28 are then no longer activated, rather the next pair of light-emitting elements angularly offset by 45° in the clock-wise direction are activated.

This demonstrates the effective, ergonomic and economic light supply of the video endoscope 10.

It can be seen from FIG. 1 that in the course of this rotary movement an intermediate state can result in which the cross section of the optical waveguide 50 is still situated partly in the region of the light-emitting element 26, but partly already covers the circumferentially next element. This intermediate state can then be handled in such a way that in this transition region the two adjacent light-emitting elements are activated, that is to say both the element 26 and the element adjacent thereto. In terms of control technology this can be realized by virtue of the fact that in this transition state the position indicator 58 has just left the detection region of the position sensor 34 and enters into the detection region of the circumferentially next position sensor.

After use, the two components of the video endoscope 10 can be decoupled very simply by pressing the lever latch 62 on the opposite side to the latching lug 64; as a result, the latching lug 64 lifts up from the groove 38, and endoscope part 12 and light supplying part 14 can be separated from one another or pulled apart from one another.

This locking possibility is only one possibility; it is also possible, if desired, to realize a latching between the outer side of the pin 46 and the inner side of the cavity 24, such that the outer side is not occupied spatially by the latching mechanism. These latches can be spring or ball latches or the like.

Figure 3:
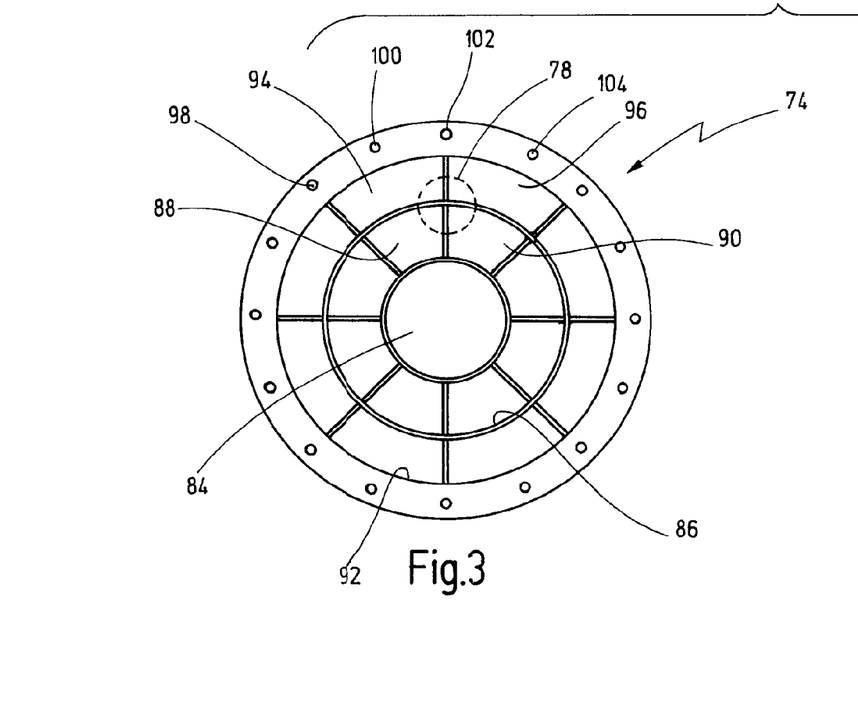
FIG. 3 shows a frontal view of the distal coupling end of a second embodiment of a light supplying part.
Figure 4:
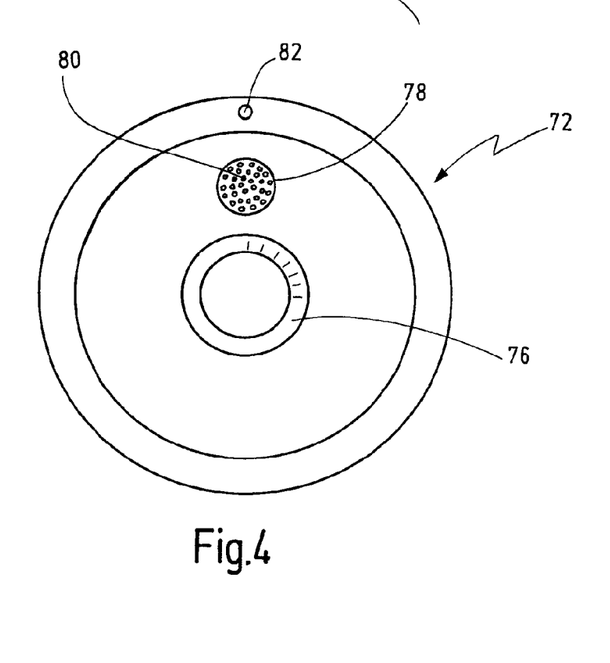
FIG. 4 shows a corresponding proximal end-side frontal view of the coupling area of an endoscope part which can be coupled to the light supplying part from FIG. 3 to form a second embodiment of a video endoscope.

FIGS. 3 and 4 illustrate a second embodiment of a video endoscope, which is provided in its entirety with the reference numeral 70.

This video endoscope 70 also has an endoscope part 72 and a light supplying part 74. The respective coupling-side ends of the components endoscope part 72 and light supplying part 74 can be seen in the illustration in FIGS. 3 and 4.

As described above, the central pin 76 projects from the endoscope part 72, the optical assembly being accommodated in said pin.

In this exemplary embodiment, only a single optical waveguide 78 is present on the endoscope part 72, said optical waveguide being composed of a fibre bundle 80 of individual optical fibres. A position indicator 82 is present on the outer edge here, too.

As can be seen from FIG. 3, the light supplying part 74 again has a central cavity 84, into which the pin 76 can be pushed in a matching manner.

A first ring 86 is present around the cavity 84, said ring 86 being composed of eight individual segment-like light-emitting elements, only the two light-emitting elements 88 and 90 being provided with a reference numeral here.

A second ring 92 is placed coaxially around the first illumination ring, said second ring 92 being composed of eight individual segment-like light-emitting elements, likewise only the two elements 94 and 96 being provided with a reference symbol here.

A total of sixteen position sensors are arranged around the outer illumination ring, only the position sensors 98, 100, 102 and 104 being provided with a reference numeral here.

In terms of circuitry, the matter can be configured in such a way that the position sensor 98 detects for the element 94, the position sensor 100 for the element 88, the position sensor 102 for the element 96, and the position sensor 104 for the element 90.

If endoscope part 72 and light supplying part 74 are coupled to one another in the positions illustrated in FIGS. 3 and 4, then the cross-sectional area of the optical waveguide 78 is located on a total of four light-emitting elements, namely on the adjacent light-emitting elements 88 and 90 of the inner illumination ring and the light-emitting elements 94 and 96 of the outer illumination ring (see dashed circle in FIG. 3).

As described above, this position can be detected by means of the position indicator 82, such that the four light-emitting elements 88, 90, 94 and 96 are then activated in this case.

If the endoscope part 72 is rotated somewhat in the clockwise direction, for example, then a situation occurs in which the cross section of the optical waveguide 78 is only located on the light-emitting elements 90 of the inner ring and 96 of the outer ring.

This, too, can again be detected by the position sensors, such that only these two light-emitting elements 90 and 96 are then activated.

This again not only shows the particularly economic illumination light guiding and activation, but also opens up further possibilities. Thus in the case of such a configuration with a plurality of rings, it is possible to employ a plurality of light-emitting elements of different colors. This can be expedient in the case of a photodynamic diagnosis, for example, if, for example, on one occasion only white light is intended to be employed in order to generally inspect the examination region, but then for a photodynamic diagnosis, for example, only a red or blue light is intended to be radiated in, in order to identify a specially prepared tissue, usually a tumor tissue.

This can now be realized in a simple manner by virtue of the light-emitting elements being for example LEDs or alternatively OLEDs which emit radiation in different colors.

If, by way of example, the optical waveguide 78 is situated in the somewhat rotated position described above in which it covers only the two light-emitting elements 96 and 90, one of the light-emitting elements could be operated only with white light, but the other with a colored light, such that different light can be employed alternately in a specific location. Corresponding circuits or keyboards are then provided in order to realize or control this.

It is conceivable that the endoscope part 12 from FIG. 2 can also be pushed into the light supplying part 74 from FIG. 3. Depending on the position of the optical waveguides 50 and 52 of the endoscope part 12, they come into contact, for example, exclusively with the region of light-generating elements of the first inner ring 86 or of the second outer ring 92. The position of the optical waveguides 50 and 52 can also be chosen in such a way that one is always aligned only with the optical waveguides of the outer ring, and the other only with the optical waveguides of the inner ring. It is possible to effect switching in such a way that one optical waveguide 50 can be operated with white light, for example, and the second optical waveguide 52 with an illumination light suitable for a photodynamic diagnosis.

This again shows the high flexibility of the video endoscope coupling system.

Figure 5:
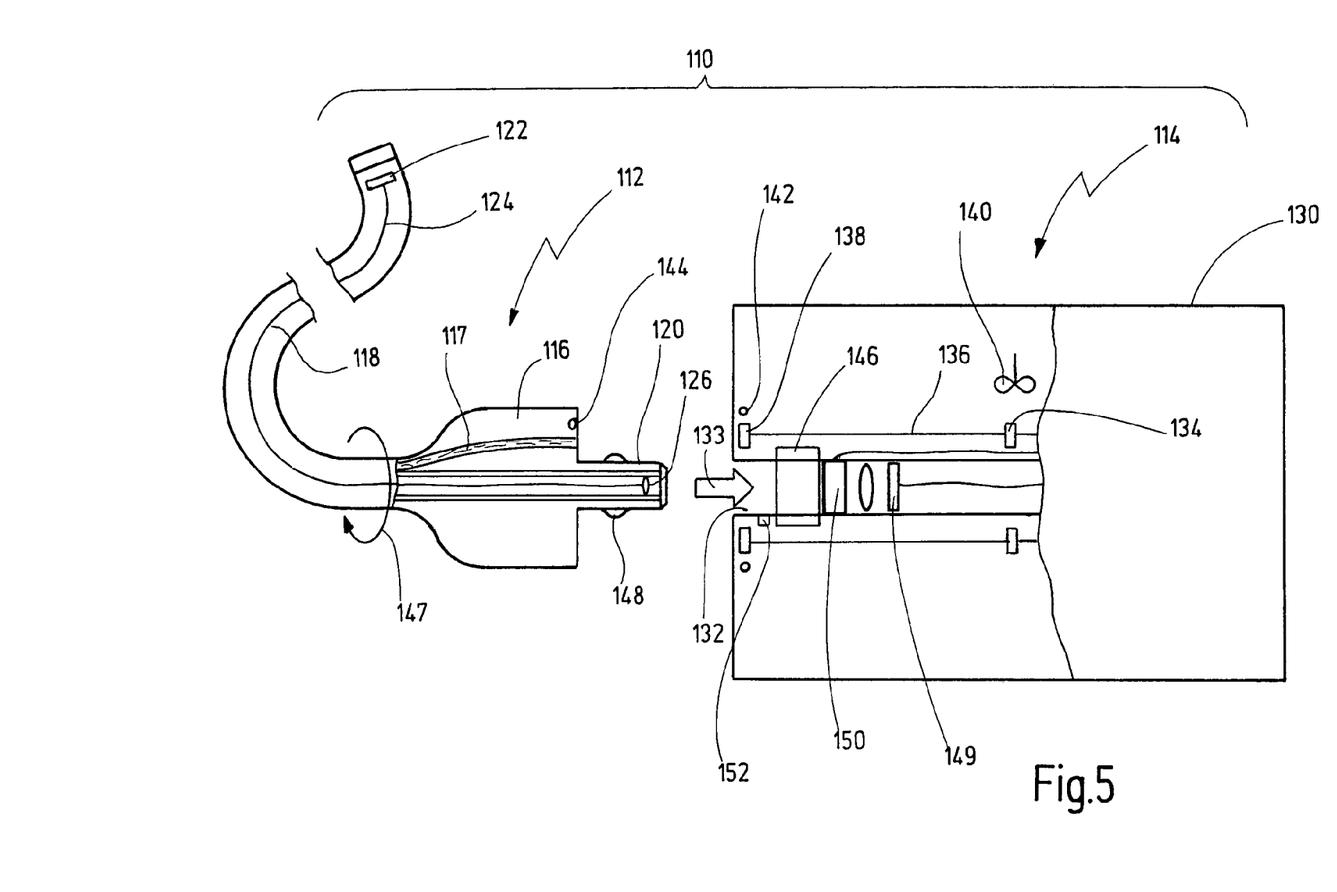
FIG. 5 shows highly schematically a third embodiment of a video endoscope, wherein the light supplying part is embodied as a standing unit and the endoscope part is embodied as a flexible endoscope.

FIG. 5 illustrates a third embodiment of a video endoscope, which is designated in its entirety by the reference numeral 110.

The video endoscope 110 has an endoscope part 112 and a light supplying part 114.

The endoscope part 112 is embodied as a flexible endoscope and has a head 116, which merges into a flexible shaft 118. A pin 120 again projects from the head 116, said pin having the task or function described above. Here, too, a flexible optical waveguide 117 is led as far as the coupling area on the head 116.

In the embodiment illustrated, the endoscope part 112 is embodied as a video endoscope. In other words, an electrical image converter 122 is arranged in the region of its distal end, which electrical image converter converts the incident optical signal into an electrical signal. Said electrical signal is passed via a line 124 as far as a connection 126 in the pin 120.

The light supplying part 114 is configured as a standing unit 130.

Here, too, a cavity 132 is present into which, as described above, the pin 120 of the endoscope part 112 can be pushed, as indicated by an arrow 133. A respective light-emitting element 138 is constructed in the standing unit 130 in such a way that it is connected to a semiconductor light source 134, lying further in the interior of the unit 130, via an optical waveguide 136. This opens up the possibility, particularly when there are numerous and light-intensively emitting semiconductor light sources 134, of cooling the latter by means of a cooling system 140.

The light-emitting element 138 is again assigned a position sensor 142, which interacts with the corresponding position indicator 144 on the endoscope part 112, as was described above.

A drive 146 is arranged in the region of the cavity 132, by means of which drive an endoscope part 112 inserted into the standing unit 130 can be rotated, as is represented by an arrow 147.

In order that an endoscope part that optically conducts the image can be pushed into the light supplying part 114, an electrical image converter 149 is provided.

In order that the light supplying part 114 can also be coupled to those endoscopes that are already embodied as a video endoscope, a connector 150 is provided in the region of the cavity 132 in order to correspondingly forward the electrical signal from the connection 126 of the endoscope part 112.

That also shows the high flexibility of the construction, that is to say the light supplying part 114 can be coupled to different types of endoscope.

A reading element 152 is arranged in the cavity 132, which reading element can read corresponding information, for example from an identification element on the pin 120.

Spring-elastic latches 148 are provided here on the outer side of the pin 120, said latches permitting latching with the drive 146, for example.

This not only ensures protection against detachment, but also equally provides a connection mechanically fixed against rotation between the pin 120 and the drive 146.

The closing and release of the coupling between endoscope part 112 and light supplying part 114 functions in the manner described above, that is to say insertion or detachment of the pin 120 in or from the standing unit 130.

The invention claimed is:

1. A video endoscope comprising
   an endoscope part having at a proximal end thereof
      a central image signal conductor,
      at least one optical waveguide, and
   a light supplying part which can be coupled to said proximal end of said endoscope part, said light supplying part has
      a central image signal conductor connection at a distal end thereof, and
      a light supply arranged coaxially around said central image signal conductor connection in a coupling area of said light supplying part,
   said endoscope part and said light supplying part are rotatable with respect to one another when coupled, wherein
   said light supply has a plurality of light-emitting elements arranged around said central image signal conductor connection, each of said light-emitting elements can be supplied by means of a switchable semiconductor light source; and wherein
   position sensors are arranged in an area of said light-emitting elements, and
   position indicators are arranged on said endoscope part in an area of said at least one optical waveguide,
   a position of said position indicators can be detected by said position sensors when said endoscope part and said light supplying part are coupled, and wherein, based on a detection of said position indicator by a position sensor, at least these light-emitting elements lying opposite to said optical waveguide are activated.

2. The video endoscope of claim 1, wherein only those light-emitting elements which lie in a cross-sectional area of said optical waveguide of said endoscope part are activated.

3. The video endoscope of claim 1, wherein said light-emitting elements are designed in segment-like fashion.

4. The video endoscope of claim 3, wherein said light-emitting elements are combined to form at least one ring.

5. The video endoscope of claim 1, wherein said switchable semiconductor light sources are selected from the group consisting of LEDs, OLEDs, diode lasers or combinations thereof.

6. The video endoscope of claim 1, wherein said switchable semiconductor light source directly forms said light-emitting element.

7. The video endoscope of claim 1, wherein said switchable semiconductor light sources are arranged at an axial distance from said light-emitting elements situated on one end side, and are connected to said light emitting via optical waveguides.

8. The video endoscope of claim 1, wherein said light-emitting elements emit light of different colors.

9. The video endoscope of claim 1, wherein said semiconductor light sources are accommodated in a separate apparatus.

10. The video endoscope of claim 1, wherein a cooling system for cooling said semiconductor light sources are present.

11. The video endoscope of claim 1, wherein said position sensors and said position indicators are designed as Hall sensors.

12. The video endoscope of claim 1, wherein said endoscope part has an identification element which can be read by means of a reading element arranged at said light supplying part.

13. The video endoscope of claim 1, wherein a latching mechanism is provided, which provides a latching of said endoscope part and said light supplying part when coupled one to another.

14. The video endoscope of claim 13, wherein said latching mechanism is embodied in such a way that it is possible for said endoscope part to rotate about said light supplying part into positions with equidistant angular distances.

15. The video endoscope of claim 1, wherein said endoscope part has a control element, by means of which, when said light supplying part is detected, said endoscope part can be rotated about said light supplying part.

16. The video endoscope according of claim 1, wherein said light supplying part is a camera part with an electrical image converter.

17. The video endoscope of claim 1, wherein an electrical image converter is integrated in said endoscope part, and wherein a connector part is provided in said light supplying part, by means of which connector part said electrical image signal can be forwarded.

18. The video endoscope of claim 1, wherein said light supplying part is a standing unit, into which said endoscope part can be inserted.

19. The video endoscope of claim 1, wherein a drive is present in said light supplying part, by means of which drive a coupled endoscope part can be rotated.

20. The video endoscope of claim 1, wherein said endoscope part has a central, proximally projecting pin which accommodates said image signal conductor.

21. The video endoscope of claim 20, wherein said central image signal conductor connection of said light supplying part has a cavity, into which said projecting pin can be inserted.

* * * * *